(12) United States Patent
Hoffmann

(10) Patent No.: US 6,358,924 B1
(45) Date of Patent: Mar. 19, 2002

(54) GLP-1 FORMULATIONS

(75) Inventor: James Arthur Hoffmann, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/585,181

(22) Filed: Jun. 1, 2000

Related U.S. Application Data

(63) Continuation of application No. PCT/US98/25515, filed on Dec. 2, 1998.
(60) Provisional application No. 60/067,600, filed on Dec. 5, 1997.

(51) Int. Cl.$^7$ ........................ A61K 38/26; C07K 14/605
(52) U.S. Cl. ........................ 514/12; 514/21; 530/324
(58) Field of Search .................... 514/12, 21; 530/324, 530/399

(56) References Cited

U.S. PATENT DOCUMENTS

| | | | |
|---|---|---|---|
| 5,120,712 A | 6/1992 | Habener | 514/12 |
| 5,376,637 A | 12/1994 | Sawai et al. | 514/12 |
| 5,512,549 A | 4/1996 | Chen et al. | 514/12 |
| 5,545,618 A | 8/1996 | Buckley et al. | 514/12 |
| 5,705,483 A | 1/1998 | Galloway et al. | 514/12 |
| 5,766,620 A | 6/1998 | Heiber et al. | 424/436 |
| 5,811,388 A | 9/1998 | Friend et al. | 514/2 |
| 2001/0011071 A1 * | 8/2001 | Knudsen et al. | 514/12 |

FOREIGN PATENT DOCUMENTS

| | | |
|---|---|---|
| EP | 619 322 | * 10/1994 |
| WO | 93/18785 | 9/1993 |
| WO | 97/31943 | 9/1997 |
| WO | WO 99/47160 | 9/1999 |

* cited by examiner

*Primary Examiner*—Jeffrey E. Russel
(74) *Attorney, Agent, or Firm*—Mark J. Stewart; Gregory A. Cox

(57) ABSTRACT

Methods and formulations are presented that provide for a) the oral absorption of GLP-1 peptides that bind surfactants; and b) long-term storage of formulations containing these peptides. For example, a GLP-1/DSS complex is administered orally instead of parenterally, which is much more convenient for, and facilitates compliance with diabetic patients and persons with other GLP-1 treated conditions.

11 Claims, No Drawings

GLP-1 FORMULATIONS

RELATED APPLICATIONS

This application is a continuation of International Application Serial No. PCT/US98/25515, filed Dec. 2, 1998, which claims the benefit of U.S. Provisional Application No. 60/067,600, filed Dec. 5, 1997. The entire teachings of these prior applications are incorporated herein by reference.

BACKGROUND OF THE INVENTION

Formulations are presented that have improved storage characteristics. These formulations are particularly suitable for oral absorption of GLP-1 peptides that bind surfactants.

Administration of therapeutic peptides is often limited to parenteral routes rather than preferred oral administration due, e.g. to destruction of the peptides if ingested rather than injected. This is unfortunate because many peptides have proven clinically effective and could have more widespread use if easy to administer and acceptable to recipients. For example, GLP-1-like molecules possess anti-diabetic activity in human subjects suffering from Type II and, in some cases, even Type I diabetes. Treatment with GLP-1 elicits activity (increased insulin secretion and biosynthesis, reduced glucagon secretion, delayed gastric emptying) only at elevated glucose levels, and thus provides a potentially much safer therapy than insulin or sulfonylureas. Postprandial and glucose levels in patients can be moved toward normal levels with proper GLP-1 therapy. There are also reports suggesting GLP-1-like molecules possess the ability to preserve and even restore pancreatic beta cell function in Type-II patients. On the other hand, to be effective as a treatment, GLP-1 formulations may have to be administered by injection at, or slightly before, each meal. This is the regimen used to administer insulin. For such a regimen, a multi-use solution formulation stored for long periods of time at refrigerated or ambient temperature is preferred. Such a formulation must contain a preservative with sufficient anti-microbial properties to prevent degradation and contamination of the solution. Unfortunately, preservatives tend to deleteriously affect the therapeutic agent, e.g. a peptide. For example, solutions of GLP-1 molecules undergo conformational changes in the presence of a preservative such as phenol. In the presence of the preservative meta-cresol (m-cresol), aqueous solutions of GLP-1 molecules that are near neutral pH turn hazy, and precipitation develops. What is needed therefore, are additives for formulations of peptides such as GLP-1 molecules that allow storage at refrigeration (about 4° C. or lower) and/or ambient temperatures while still preserving both solution clarity, compound integrity, and biological activity.

SUMMARY OF THE INVENTION

Methods and formulations of the present invention provide formulations for a. oral absorption of GLP-1 peptides that bind surfactants with high affinity; b. long term storage of formulations containing these peptides.

An aspect of the invention is a formulation comprising a GLP-1 peptide and a small quantity of a surfactant. Preferred surfactants include DSS (docusate sodium, CAS Registry Number [577-11-7]) and related substances; docusate calcium [CAS number 128-49-4], and docusate potassium [CAS number 7491-09-0]. Other surfactants include SDS (sodium dodecyl sulfate or sodium lauryl sulfate), sodium caprylate, sodium cholate, sodium deoxycholate, sodium taurocholate, and sodium glycocholate. Suitable agents also include zwitterionic (e.g. N-alkyl-N,N-dimethylammonio-1-propanesulfonates, 3-cholamido-1-propyldimethylammonio-1-propane-sulfonate), cationic (cetylpyridinium chloride), non-ionic (Triton X-100, Dodecyl β-D-glucopyranoside), or polymeric (Tween-40, Tween-80, Brij-35) surfactants.

Peptides used in the formulations of the present invention include GLP-1 or GLP-1-like molecules. A preferred GLP-1-like molecule is $Val^8$-GLP-1. Other suitable GLP-1-like molecules include the 2 native GLP-1 forms, position-8 analogs, and molecules containing a C-terminal acid.

The formulation is stable at a pH of about 6.5 to 9.0, more preferably at a pH of about 7 to 8. The formulation includes a preservative. Preferred preservatives include m-cresol, phenol, methylparaben, and benzyl alcohol. The formulation is stable during long term storage at 4° C. and ambient temperature. The formulation optionally includes an isotonicity agent, for example glycerin, or sodium chloride.

Another aspect of the invention is a method of treating a person having diabetes or other conditions in which the administration of a GLP-1-like molecule is indicated. The method includes obtaining a formulation of the present invention and administering a pharmacologically effective amount of the formulation to the person. Preferably an oral route is used to administer the formulation, although a parenteral route is also suitable.

DETAILED DESCRIPTION OF THE INVENTION

Methods and formulations of the present invention provide for a) the oral absorption of GLP-1 peptides that bind surfactants with high affinity; and b) long-term storage of preserved formulations containing these peptides. In an embodiment of the invention, a GLP-1/DSS complex is used to administer GLP-1 orally instead of parenterally. This aspect of the invention provides much greater convenience and compliance for diabetic patients and persons having other conditions in which treatment with a GLP-1-like molecule is indicated. This characteristic will make GLP-1 treatment more useful and widely available. Use of preservatives prevents microbial contamination and therefore allows multiple use from a single solution.

Several key observations suggest that a significant portion of a GLP-1 peptide in a formulation containing sodium docusate (DSS) will be absorbed orally:

a. DSS binds to GLP-1 with a high affinity;

b. DSS binding alters GLP-1 secondary structure; this altered structure may correspond to a membrane-transportable state as described by Milstein (1996). The DSS appears to be acting as a so-called carrier molecule.

c. After administration of the formulation into a body (subcutaneously) the GLP-1 peptide exhibits full biological activity; this suggests either that the GLP-1 in the formulation retains its receptor binding affinity or the GLP-1-DSS complex in the formulation can be disrupted, reforming the native GLP-1 in an alpha-helix structure; a CD study showed that a 2-day dialysis of a GLP-1-DSS mixture did not revert the GLP-1 back to its alpha-helix conformation.

d. Large quantities of DSS can be safely administered orally because it is already approved for use as a laxative in humans; some of the orally administered DSS is absorbed systemically.

The addition of an anionic surfactant sodium docusate (DSS), at a very low level (2:1 on a molar basis vs. peptide), also dramatically improved the solution stability of Val$^8$-GLP-1(7-37)OH in a formulation that is isotonic, is at a near neutral pH (pH 7.8), and also contains a suitable preservative (m-cresol). This formulation provides an improved product that should meet antimicrobial-sterility standards throughout the world. Improvement in formulation stability is over a wide range of storage conditions, from about 2° C. to about 37° C., more preferably at about 4° to about 25° C.

In an embodiment, the formulation allows single or multi-use parenteral formulation of a GLP-1 analog to be prepared that is suitable for long-term storage. Also, because the DSS facilitates the GLP-1 existing in a soluble micelle or aggregated state, this formulation provides an improved prolonged time action after subcutaneous administration.

The anionic surfactant, sodium docusate (DSS) has a very high affinity for a GLP-1 compound, specifically Val$^8$-GLP-1(7-37)OH and, upon binding to the peptide, the Val$^8$-GLP-1 secondary structure is converted from mostly alpha-helix to mostly a beta sheet. A slightly larger form of Val$^8$-GLP-1 with DSS molecule(s) bound to it was observed on size-exclusion chromatography (SEC) and the altered secondary structure was noted by circular dichroism experiments (CD).

A formulation containing DSS and Val$^8$-GLP-1 injected subcutaneously into dogs showed insulinotropic-like activity comparable in potency to Val$^8$-GLP-1 in a phosphate buffer solution (PBS formulation).

Preferred embodiments for a surfactant include DSS (docusate sodium, CAS Registry Number [577-11-7]) and related substances; docusate calcium [CAS number 128-49-4], docusate potassium [CAS number 7491-09-0].

Also preferred are other surfactants including: SDS (sodium dodecyl sulfate or sodium lauryl sulfate), sodium caprylate, sodium cholate, sodium deoxycholate, sodium taurocholate, and sodium glycocholate.

Other suitable surfactants include: zwitterionic (e.g. N-alkyl-N,N-dimethylammonio-1-propanesulfonates, 3-cholamido-1-propyldimethylammonio-1-propane-sulfonate), cationic (cetylpyridinium chloride), non-ionic (Triton X-100, Dodecyl β-D-glucopyranoside), or polymeric (Tween-40, Tween-80, Brij-35) surfactants.

Preferred preservatives include m-cresol and phenol. Also preferred are methylparaben, benzyl alcohol, and other similar preservatives.

A preferred isotonicity agent is glycerin, also preferred is any isotonicity agent (e.g. sodium chloride).

Optionally, a wide range of excipients may be included in the formulation, such as glycerin, m-cresol, phenol, methylparaben, and the like, although the excipients alone would not provide the dramatic improvement in solution stability that characterizes the present invention. Some of these excipients are preservatives, some are isotonicity agents.

GLP-1-like molecules include GLP-1 analogs and derivatives, GLP-1 molecules, native as well as GLP-1 analogs, that bind tightly (that is, with high affinity) with surfactants. A preferred GLP-1 molecule is: Val$^8$-GLP-1.

GLP-1 molecules such as native GLP-1(7-36)NH2 and GLP-1(7-37)OH, as well as other GLP-1 analogs are also suitable for the practice of the invention. Also preferred are position-8 analogs and analogs containing a C-terminal acid. All other analogs are also suitable if they bind with high affinity to surfactants.

"GLP-1" means GLP-1(7-37). By custom in the art, the amino-terminus of GLP-1(7-37) has been assigned number 7 and the carboxy-terminus has been assigned number 37. The amino acid sequence of GLP-1(7-37) is well-known in the art, but is presented as SEQ ID NO:1 for the reader's convenience.

A "GLP-1 analog" is defined as a molecule having one or more amino acid substitutions, deletions, inversions, or additions compared with GLP-1. GLP-1 analogs known in the art include, for example, GLP-1(7-34), GLP-1(7-35), GLP-1(7-36), Val$^8$-GLP-1(7-37), Gln$^9$-GLP-1(7-37), D-Gln$^9$-GLP-1(7-37), Thr$^{16}$-Lys$^{18}$-GLP-1(7-37), and Lys-$^{18}$-GLP-1(7-37).

A "GLP-1 derivative" is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is C$_{(1)}$–C$_{(4)}$ alkyl. Furthermore, one or more side groups, or terminal groups, may be protected by protective groups known to the ordinarily-skilled protein chemist. The α-carbon of an amino acid may be mono- or di-methylated.

The use in the present invention of a molecule claimed in U.S. Pat. No. 5,120,712, GLP-1(7-37)OH, which is expressly incorporated by reference, is highly preferred. Such molecule is selected from the group consisting of a peptide having the amino acid sequence of SEQ ID NO: 1 and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

A preferred group of GLP-1 analogs and derivatives for use in the present invention is composed of the various GLP-1 molecules claimed in U.S. Pat. No. 5,545,618, which is herein expressly incorporated by reference.

A preferred group of GLP-1 analogs and derivatives for use in the present invention is composed of molecules of formula:

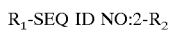

R$_1$-SEQ ID NO:2-R$_2$ and the pharmaceutically-acceptable salts thereof, wherein: R$_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine; and R$_2$ is selected from the group consisting of NH$_2$, and Gly-OH.

Numerous such GLP-1 analogs and derivatives have been disclosed and include, for example: GLP-1(7-36)NH$_2$, Gly$^8$-GLP-1(7-36)NH$_2$, Gln$^9$-GLP-1(7-37), D-Gln$^9$-GLP-1(7-37), acetyl-Lys$^9$-GLP-1(7-37), Thr$^9$-GLP-1(7-37), D-Thr$^9$-GLP-1(7-37), Asn$^9$-GLP-1(7-37), D-Asn$^9$-GLP-1(7-37), Ser$^{22}$-Arg$^{23}$-Arg$^{24}$-Gln$^{26}$-GLP-1(7-37), Thr$^{16}$-Lys$^{18}$-GLP-1(7-37), Lys$^{18}$-GLP-1(7-37), Arg$^{23}$-GLP-1(7-37), Arg$^{24}$-GLP-1(7-37), and the like (see, e.g., WO 91/11457).

Another preferred group of active compounds for use in the present invention is disclosed in WO 91/11457, and consists essentially of GLP-1(7-34), GLP-1(7-35), GLP-1

(7-36), or GLP-1(7-37), or the amide form thereof, and pharmaceutically-acceptable salts thereof, having at least one modification selected from the group consisting of:

(a) substitution of at least one of the following glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of the following: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of the following: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of at least one of the following: glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, (Mentlein et al. 1993), administration of GLP-1 analogs and derivatives that are protected from the activity of DPP IV is preferred, and the administration of Gly$^8$-GLP-1(7-36)NH$_2$, Val$^8$-GLP-1(7-37)OH, α-methyl-Ala$^8$-GLP-1(7-36)NH$_2$, and Gly$^8$-Gln$^{21}$-GLP-1(7-37)OH, or pharmaceutically-acceptable salts thereof, is more preferred.

Another preferred group of molecules for use in the present invention consists of compounds, claimed in U.S. Pat. No. 5,512,549, which is expressly incorporated, herein by reference. This group is defined by the general formula:

and pharmaceutically-acceptable salts thereof, wherein R$_1$ is selected from the group consisting of 4-imidazopropionyl, 4-imidazoacetyl, or 4-imidazo-α,α dimethyl-acetyl; R$_2$ is selected from the group consisting of Gly-OH or NH$_2$. In addition, Lys at position 27 of SEQ ID NO:3 may be an acyl group selected from the group consisting of C$_6$–C$_{10}$ unbranched acyl or may be absent.

More preferred compounds of SEQ ID NO:3 for use in the present invention are those in which Xaa is Arg and Lys at position 27 is C$_6$–C$_{10}$ unbranched acyl.

Highly preferred compounds of SEQ ID NO:3 for use in the present invention are those in which Xaa is Arg, Lys at position 27 is C$_6$–C$_{10}$ unbranched acyl, and R$_2$ is Gly-OH.

More highly preferred compounds of SEQ ID NO:3 for use in the present invention are those in which Xaa is Arg, Lys at position 27 is C$_6$–C$_{10}$ unbranched acyl, R$_2$ is Gly-OH, and R$^1$ is 4-imidazopropionyl.

The most preferred compound of SEQ ID NO:3 for use in the present invention is that in which Xaa is Arg, Lys at position 27, is C$^8$ unbranched acyl, R$_2$ is Gly-OH, and R$^1$ is 4-imidazopropionyl.

The use of GLP-1(7-36) amide, SEQ ID NO: 4, or a pharmaceutically-acceptable salt thereof, in the present invention is also highly preferred. The use of Val$^8$-GLP-1(7-37)OH, SEQ ID NO:5, or a pharmaceutically-acceptable salt thereof, in the present invention is most highly preferred.

Other non-GLP-1 related peptides that bind DSS may also be made orally absorbable by the methods and formulations of the present invention. To determine whether these peptides are candidates for the formulations presented herein, it is useful to determine whether they bind with high affinity to a surfactant and upon binding undergo a significant alteration of secondary structure. Suitable for practice of the invention are other DSS-like molecules (anionic surfactants like SDS); a wide range of DSS:GLP-1 ratios, for example, 0.1 to 1 to 20:1 or 50:1; a wide range of formulation conditions (pH, other non-active excipients, glycerin, alcohol, polymeric additives, coatings, and the like); tablet, liquid or capsule forms; and the like. (Remington's "Pharmaceutical Sciences," 1980).

EXAMPLES

The following examples are presented to exemplify, not limit the invention.

Example 1

Preserved Formulations of Val$^8$-GLP-1 (7-37)OH with DSS

A formulation of the invention was prepared by dissolving Val$^8$-GLP-1(7-37)OH at 1 mg/ml in an aqueous solution containing 16 mg/ml glycerin and 10 mM sodium tribasic phosphate. The solution was adjusted to about pH 8.1 using 1N HCl.

The preservative m-cresol was prepared at a concentration of 100 mg/ml in absolute ethanol.

Sodium docusate (DSS) was prepared at a concentration of 20 mg/ml in water with gentle warming on a hot plate.

To each of 500 μL aliquots of the Val$^8$-GLP-1(7-37)OH solution in 3-ml glass vials were added 0, 3.3, 6.6 or 16.5 μL of the DSS solution followed by 15.8 μL of the preservative m-cresol solution. After gentle mixing of the components in the vials by hand swirling the pH of each clear solution was-adjusted to pH 7.8. Replicate samples were incubated at 4° C., ambient temperature, and 37° C. Within 4 hours at ambient temperature, the samples containing 0 or 3.3 μL of the DSS solution had become hazy due to peptide denaturation.

After incubation for 16 hours at 37° C., all four types of samples were clear. The solutions were then incubated at 4° C. Again, the solutions containing 0 or 3.3 μL of the DSS solutions became, and remained, hazy.

The solutions containing 6.6 μL or 16.5 μL of the DSS solution, which correspond to 2:1 and 10:1 molar ratios DSS to Val$^8$-GLP-1(7-37)OH, respectively, remained clear at 4° C. for at least 6 weeks. At this time, HPLC analysis showed a purity of the Val$^8$-GLP-1(7-37)OH of 98.3% and 97.2%, respectively.

Example 2

A Preserved Formulation of Val$^8$-GLP-1 (7-37)OH with DSS

A formulation of the invention was prepared by dissolving Val$^8$-GLP-1(7-37)OH at about 1.0 mg/ml in an aqueous solution containing 16 mg/ml glycerin and 10 mM sodium tribasic phosphate. The solution was adjusted to about pH 8.0 using 5N HCl. The solution was then filtered through 0.2$\mu$ and 0.02$\mu$ filters. The peptide concentration was quantified by ultraviolet (UV) analysis at 280 nm.

6.5 ml of the Val$^8$-GLP-1 solution was added to 1.62 mg of solid DSS, which had been dried from a 100 mg/ml solution in absolute ethanol, to give a 2:1 molar ratio of DSS to Val$^8$-GLP-1. After gently stirring 15 minutes at ambient temperature the solution was added to 20.5 mg of m-cresol, which had been dried from a 100 mg/ml solution in absolute ethanol, to give a m-cresol concentration of about 3.15 mg/ml. After stirring 15 minutes at ambient temperature, the solution was adjusted to about pH 7.7 and passed through a 0.2$\mu$ filter. Portions of this formulation were stored at 4° C. and at ambient temperature.

After 18 weeks, the formulations maintained at 4° C. and at ambient temperature were examined. Both solutions were clear. At this time, HPLC analysis showed a purity of the Val$^8$-GLP-1(7-37)OH of 98.3% and 90.8% for the 4° C. and ambient temperature samples, respectively.

Example 3

In Vivo Effects of a Formulation

A portion of the formulation from Example 2 was injected subcutaneously into beagle dogs that were clamped at an elevated glycemic level (200 mg/dl). 3 nmoles/kg of Val$^8$-GLP-1 were injected into each animal. Glucose infusion rates needed to maintain hyperglycemia were measured for 2.5 hours after the injections and compared to injections of a vehicle control solution.

In comparison to the vehicle control, the injection of the Val$^8$-GLP-1 formulation resulted in an elevated glucose infusion for about two hours post-injection, indicating appropriate biological activity of the peptide is maintained under these conditions.

Example 4

Preserved Formulations of Val$^8$-GLP-1 with Other Surfactants

A formulation of the invention was prepared by dissolving Val$^8$-GLP-1(7-37)OH at 1 mg/ml in an aqueous solution containing 16 mg/ml glycerin and 10 mM sodium tribasic phosphate. The solution was adjusted to about pH 8.0 using 2N HCl.

The preservative m-cresol was prepared at a concentration of 100 mg/ml in absolute ethanol.

Various formulation excipients listed herein were added to 500 $\mu$L aliquots of the Val$^8$-GLP-1(7-37)OH solution in 3-ml glass vials. After stirring for about 45 minutes at ambient temperature, 15.8 $\mu$l of a 100 mg/ml m-cresol solution in absolute ethanol was added to give a m-cresol concentration of about 3 mg/ml. The test solutions were observed for clarity for about 3 hours at ambient temperature and then at 4° C. overnight.

Without any additives, the Val$^8$-GLP-1 solution becomes hazy at both ambient temperature and at 4° C. Addition of the following surfactants preserved solution clarity at ambient temperature, but not at 4° C.: 10 $\mu$l of Tween-40, 10 $\mu$l of Tween-80. Hence these surfactants did improve formulation stability.

---

What is claimed is:

1. A stable pharmaceutical formulation comprising a GLP-1 compound selected from the group consisting of: GLP-1, GLP-1 analogs, and GLP-1 derivatives wherein the GLP-1 compound can bind to the GLP-1 receptor, complexed with an anionic surfactant selected from the group consisting of docusate sodium, docusate calcium, docusate potassium, sodium dodecyl sulfate, sodium caprylate, sodium cholate, sodium deoxycholate, sodium taurocholate, and sodium glycocholate and a preservative wherein the stable formulation is a solution and has a pH between about 6.5 and about 9.0.

2. The formulation of claim 1, wherein the GLP-1 compound is a GLP-1 derivative.

3. The formulation of claim 2, wherein the GLP-1 derivative is a GLP-1 analog having an acylated lysine $\epsilon$-amino group.

4. The formulation of claim 1, wherein the GLP-1 compound has an amino acid sequence selected from the group consisting of SEQ ID NO:1, SEQ ID NO:4, and SEQ ID NO:5, or pharmaceutically acceptable salts thereof.

5. The formulation of claim 1 further comprising an isotonicity agent.

6. The formulation of claim 1 wherein the anionic surfactant is docusate sodium.

7. The formulation of claim 6 wherein the GLP-1 compound is complexed with docusate sodium and has an altered secondary structure compared to the uncomplexed GLP-1 compound.

8. The formulation of claim 7 wherein the GLP-1 compound comprises the sequence of SEQ ID NO:5.

9. The formulation of claim 1 wherein the molar ratio of anionic surfactant to GLP-1 compound is between about 0.1:1 and about 50:1.

10. The formulation of claim 9 wherein the molar ratio is about 2:1.

11. A method of treating a person having a condition for which administration of a GLP-1 compound is indicated, said method comprising administering a pharmacologically effective amount of a formulation of claim 1.

* * * * *

SEQUENCE LISTING

<160> NUMBER OF SEQ ID NOS: 5

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Glu Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: synthetic contruct
<221> NAME/KEY: MISC_FEATURE
<222> LOCATION: (1)..(1)
<223> OTHER INFORMATION: Xaa at position 1 is Ala, Gly, Val, Thr, and Ile;
<221> NAME/KEY: MISC_FEATURE
<222> LOCATION: (14)..(14)
<223> OTHER INFORMATION: Xaa at position 14 is Glu, Gln, Ala, Thr, Ser, and Gly;

```
<221> NAME/KEY: MISC_FEATURE
<222> LOCATION: (20)..(20)
<223> OTHER INFORMATION: Xaa at position 20 is Glu, Gln, Ala, Thr, Ser,
      and Gly;
<221> NAME/KEY: MISC_FEATURE
<222> LOCATION: (30)..(30)
<223> OTHER INFORMATION: Xaa at position 30  is Gly or absent.

<400> SEQUENCE: 2

Xaa Glu Gly Thr Phe Thr Ser Asp Val Ser Ser Tyr Leu Xaa Gly Gln
1               5                   10                  15

Ala Ala Lys Xaa Phe Ile Ala Trp Leu Val Lys Gly Arg Xaa
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: synthetic construct
<221> NAME/KEY: MISC_FEATURE
<222> LOCATION: (19)..(19)
<223> OTHER INFORMATION: Xaa at position 19 is Lys or Arg;
<221> NAME/KEY: MISC_FEATURE
<222> LOCATION: (27)..(27)
<223> OTHER INFORMATION: Lys at position 27 may be acylated;
<221> NAME/KEY: MISC_FEATURE
<222> LOCATION: (30)..(30)
<223> OTHER INFORMATION: Xaa at position 30 is Gly or absent.

<400> SEQUENCE: 3

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
            20                  25                  30

<210> SEQ ID NO 4
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: synthetic construct

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```